United States Patent [19]
Akiyama et al.

[11] Patent Number: 5,773,828
[45] Date of Patent: Jun. 30, 1998

[54] GAS ANALYZER

[75] Inventors: Shigeyuki Akiyama; Masahiko Fujiwara; Takuji Oida; Naohito Shimizu; Aritoshi Yoneda; Toshikazu Ohnishi, all of Miyanohigashi-machi, Japan

[73] Assignee: Horiba, Ltd., Kyoto, Japan

[21] Appl. No.: 606,071

[22] Filed: Feb. 23, 1996

[30] Foreign Application Priority Data

Mar. 4, 1995 [JP] Japan ................................ 7-070593

[51] Int. Cl.$^6$ .............................................. G01N 21/35
[52] U.S. Cl. ........................................ 250/345; 250/343
[58] Field of Search .................................. 250/345, 343

[56] References Cited

U.S. PATENT DOCUMENTS

| 4,684,805 | 8/1987 | Lee et al. ................................ 250/343 |
| 4,914,719 | 4/1990 | Conlon et al. . |
| 5,331,409 | 7/1994 | Thurtell et al. ........................ 356/437 |

FOREIGN PATENT DOCUMENTS

| 205531 | 12/1983 | German Dem. Rep. . |
| 2900624 | 8/1980 | Germany . |
| 159367 | 8/1991 | Germany . |
| 52-42171 | 4/1977 | Japan . |
| 53-98889 | 8/1978 | Japan . |
| 5-72130 | 3/1993 | Japan . |
| 698023 | 10/1953 | United Kingdom . |

OTHER PUBLICATIONS

J. Staab. "Industrielle Gasanalyse". *Technisches messen* 60 (1993) 10; pp. 398–401.

*Primary Examiner*—Constantine Hannaher
*Attorney, Agent, or Firm*—Oppenheimer Wolff & Donnelly LLP

[57] ABSTRACT

A gas analyzer has a simple composition and can measure multi-components at a high accuracy. A plurality of measuring cells, including a case where the cells are different in length from each other, communicate sequentially with each other through a communication part to form a single gas path. A cut-on filter as an infrared penetration/reflection means for diffracting spectrally an infrared wavelength is provided on a light source side. A $NO_x$ measuring cell 3 having a cell length of about 60 mm and a $CO_2$ measuring cell 7 having a cell length of about 1 mm which communicate through the communication part with each other, and a capacitor microphone (an infrared-ray detector for $NO_x$) and a pyroelectric detector (an infrared-ray detector for $CO_2$) are provided on the infrared penetration and reflection sides of the optical filter.

16 Claims, 7 Drawing Sheets

GAS ANALYZER

BACKGROUND OF THE INVENTION

1. Field of the Invention

The present invention relates to a gas analyzer, and more particularly to a new non-dispersive infrared analyzer (hereinafter called the NDIR) in which a plurality of cells, including a case where the cells are different in length from each other, communicate sequentially with each other through a communication part to form a single gas path, and which can measure simultaneously two or more components to be measured at a high accuracy.

2. Description of the Prior Art

The Lambert-Beer law is applied to the measurement using a NDIR. According to the law expressed in the following equation (1), where the length of a cell is constant, the larger the absorption coefficient of a component becomes, or the higher the concentration of the component to be measured becomes, the larger the curve in a calibration curve becomes. Where the concentration of the component to be measured is constant, the longer the length of a cell becomes, the larger the curve in a calibration curve becomes.

$$I = I_0 \cdot exp(-\mu \cdot c \cdot L) \tag{1}$$

where $I_0$ is incident light intensity; c is concentration of component to be measure (amount of infrared rays absorbed in cell); $\mu$ is absorption coefficient inherent in component to be measured; I is penetrated light intensity; and L is cell length.

Thus, in the NDIR analyzer, such curve is linearized by an approximation equation, and however, the linearization has a limit due to calculation accuracy and the like.

On the other hand, the longer the cell length L is made, the higher the sensitivity becomes, so that with consideration to the sensitivity and curve, the cell length L is determined. However, there is a complicated problem that an adaptable cell length L varies depending on the component to be measured and concentration thereof. Although the above-mentioned linearization copes with the problem, if the variation cannot be corrected, the cell length L must be changed.

For example, in oil fired boilers used for electric power companies, according to a law such as a regulation of $NO_X$ as one of components to be measured, a denitration means has been employed to control $NO_X$ component to a certain concentration or less. Where the exhausting concentration of $NO_X$ is controlled to, for example, about 20 through 30 ppm, a $NO_X$ measuring range of 0 through 50 ppm is required. $CO_2$ concentration, though varies depending on combustion state, is about 14% during boiler operation, and usually a $CO_2$ measuring range of 0 through 20% is required.

Therefore, a $NO_X$ meter to measure $NO_X$ whose exhausting concentration is controlled to about 20 through 30 ppm is largely different in cell length from a $CO_2$ meter to measure $CO_2$ having a concentration of about 14%. For example, in a gas flue analyzer, the cell length is set at 60 mm to measure $NO_X$ having an exhausting concentration of about 20 through 30 ppm, and the cell length is set at 1 mm to measure $CO_2$ having a concentration of about 14%.

As described above, where two components are different in concentration from each other, they are different in adaptable cell length, so that where components to be measured are largely different in absorption intensity, detection method and measured concentration, a single cell could not cope with the difference. In order to avoid the problem, heretofore, two components have been measured at respective two benches, so that there has been a problem that a single cell having a cell length L corresponding to a component to be measured is required for each bench, and thus a plurality of measuring cells are required and a plurality of gas introducing routes (gas paths) are also required, and the composition becomes complex.

SUMMARY OF THE INVENTION

The present invention is made in view of such circumstances and it is an object of the invention to provide a gas analyzer which is simple in composition and can measure multi-components at a high accuracy.

In the present invention, a means to solve the above-mentioned problems is composed as follows.

That is, the present invention provides a gas analyzer in which a plurality of measuring cells, including a case where the cells are different in length from each other, communicate sequentially through a communication part with each other to form a single gas path, characterized in that an infrared penetration/reflection means is provided adjacently to a light source, and that at least one set of measuring cells, communicating through the above-mentioned communication part with each other and infrared-ray detectors corresponding thereto, is provided on the infrared penetration side and infrared reflection side, respectively, of the infrared penetration/reflection means.

The present invention provides a gas analyzer in which a plurality of measuring cells, including a case where the cells are different in length from each other, communicate sequentially with each other through a communication part to form a single gas path, characterized in that a first infrared penetration/reflection means is provided adjacently to a light source; that a first measuring cell and a second measuring cell which communicate through the above-mentioned communication part with each other are provided on the infrared penetration side and infrared reflection side, respectively, of the first infrared penetration/reflection means; that a second infrared penetration/reflection means is provided between the above-mentioned first measuring cell and a first infrared-ray detector is provided on the infrared reflection side of the second infrared penetration/reflection means; and that a second infrared-ray detector 9 corresponding to the second measuring cell 7 is provided.

The present invention is characterized in that a third measuring cell may be interposed between the infrared reflection side of the second infrared penetration/reflection means and the third infrared-ray detector.

The present invention provides a gas analyzer in which a plurality of measuring cells, including a case where the cells are different in length from each other, communicate sequentially with each other through a communication part to form a single gas path, characterized in that a first infrared penetration/reflection means is provided adjacently to a light source, and a second infrared penetration/reflection means is connectedly provided on the infrared penetration side of the first infrared penetration/reflection means; that a first measuring cell and a first infrared-ray detector corresponding to the first measuring cell are provided on the infrared penetration side of the second infrared penetration/reflection means; that a second measuring cell and a second infrared-ray detector corresponding to the second measuring cell are provided on the infrared reflection side of the above-mentioned first infrared penetration/reflection means; and that a third measuring cell and a third infrared-ray detector corresponding to the third measuring cell are provided on the infrared reflection side of the above-mentioned second infrared penetration/reflection means.

The present invention provides a gas analyzer in which a plurality of measuring cells, including a case where the cells are different in length from each other, communicate sequentially with each other through a communication part to form a single gas path, characterized in that a first measuring cell is provided between a light source and a first infrared penetration/reflection means; that a second infrared penetration/reflection means is provided on the infrared penetration side of the first infrared penetration/reflection means; that a first infrared-ray detector is provided on the infrared penetration side of the second infrared penetration/reflection means; that a second measuring cell and a second infrared-ray detector corresponding to the second measuring cell are provided on the infrared reflection side of the above-mentioned first infrared penetration/reflection means; and that a third measuring cell and a third infrared-ray detector corresponding to the third measuring cell are provided on the infrared reflection side of the above-mentioned second infrared penetration/reflection means.

The present invention provides a gas analyzer in which a plurality of measuring cells, including a case where the cells are different in length from each other, communicate sequentially with each other through a communication part to form a single gas path, characterized in that a first infrared penetration/reflection means is provided adjacently to a light source; that a second infrared penetration/reflection means is provided through a first measuring cell on the infrared penetration side of the first infrared penetration/reflection means; that a first infrared-ray detector and a third infrared-ray detector are provided on the infrared penetration and infrared reflection sides, respectively, of the second infrared penetration/reflection means; that a third infrared penetration/reflection means is provided through a second measuring cell on the infrared reflection side of the above-mentioned first infrared penetration/reflection means; and that a second infrared-ray detector and a fourth infrared-ray detector are provided on the infrared penetration and infrared reflection sides, respectively, of the third infrared penetration/reflection means.

The present invention provides a light-intermittent type gas analyzer in which a plurality of measuring cells, including a case where the cells are different in length from each other, communicate sequentially with each other through a communication part to form a single gas path, and which has a reference cell, characterized in that a reference cell together with a first infrared penetration/reflection means and a first measuring cell together with a second infrared penetration/reflection means are provided parallel between a light intermitter made adjacent to a light source and a two-chamber light reception type infrared-ray detector; that a first infrared-ray detector is provided on the infrared reflection side of the above-mentioned second infrared penetration/reflection means; and that a second infrared-ray detector is provided through a second measuring cell communicating with the above-mentioned first measuring cell on the infrared reflection side of the above-mentioned first infrared penetration/reflection means.

The present invention is characterized in that a third infrared penetration/reflection means may be arranged between the second infrared penetration/reflection means and the first measuring cell; that a third measuring cell communicating with the above-mentioned first measuring cell may be arranged on the infrared reflection side of the third infrared penetration/reflection means; and that a third infrared-ray detector corresponding to the third measuring cell may be provided.

The present invention is characterized in that at least one pair of infrared penetration/reflection means may be provided between the light intermitter and the reference cell that a second reference cell may be provided on the infrared reflection side of the infrared penetration/reflection means, and the above-mentioned first measuring cell and a third measuring cell communicating with the second measuring cell may be provided on the infrared reflection side of the infrared penetration/reflection means; and that there may be provided another two-chamber light reception type infrared-ray detector corresponding to the second reference cell and the third measuring cell.

The present invention provides a light-intermittent type gas analyzer in which a plurality of measuring cells, including a case where the cells are different in length from each other, communicate sequentially with each other through a communication part to form a single gas path, and which has a reference cell, characterized in that a first infrared penetration/reflection means, a reference cell and a second infrared penetration/reflection means which are serially and adjacently arranged to each other and a third infrared penetration/reflection means, a first measuring cell and a fourth infrared penetration/reflection means which are serially and adjacently arranged to each other are provided parallel between a light intermitter made adjacent to a light source and a two-chamber light reception type infrared-ray detector; and that a second measuring cell, a third measuring cell and a fourth measuring cell which communicate with the above-mentioned first measuring cell and a second infrared-ray detector, a third infrared-ray detector and a fourth infrared-ray detector which correspond to respective measuring cells are provided on the respective infrared reflection side of the above-mentioned first infrared penetration/reflection means, the second infrared penetration/reflection means and the third infrared penetration/reflection means.

The present invention is characterized in that a fifth measuring cell communicating with the above-mentioned first measuring cell and a fifth infrared-ray detector corresponding to the fifth measuring cell may be provided on the infrared reflection side of the fourth infrared penetration/reflection means arranged adjacently to the first measuring cell.

The present invention is characterized in that one or a plurality of infrared penetration/reflection means may be provided adjacently between the fourth infrared penetration/reflection means and the first measuring cell; that a measuring cell communicating with the above-mentioned first measuring cell may be provided on the infrared reflection side of the infrared penetration/reflection means; and that there may be provided an infrared-ray detector means corresponding to the measuring cell.

It is to be understood that the name and reference code of the measuring cells, infrared penetration/reflection means and infrared-ray detectors as set forth in the present invention do not standardize or specify the contents of the composition thereof, and that there is also included a case where the contents of the composition are different between the same names and between the same reference codes.

In a gas analyzer in which a plurality of measuring cells, including a case where the cells are different in length from each other, communicate sequentially with each other through a communication part to form a single gas path, the combination of the measuring cells, infrared penetration/reflection means and infrared-ray detectors allows either a fluid-modulation (gas modulation) system or a light-intermittent system to be easily formed by a single gas path, and multi-components to be measured at a high accuracy.

DETAILED DESCRIPTION OF THE PREFERRED EMBODIMENTS

With reference to the drawings, the embodiments of the present invention will be explained hereinafter.

Figure 1:
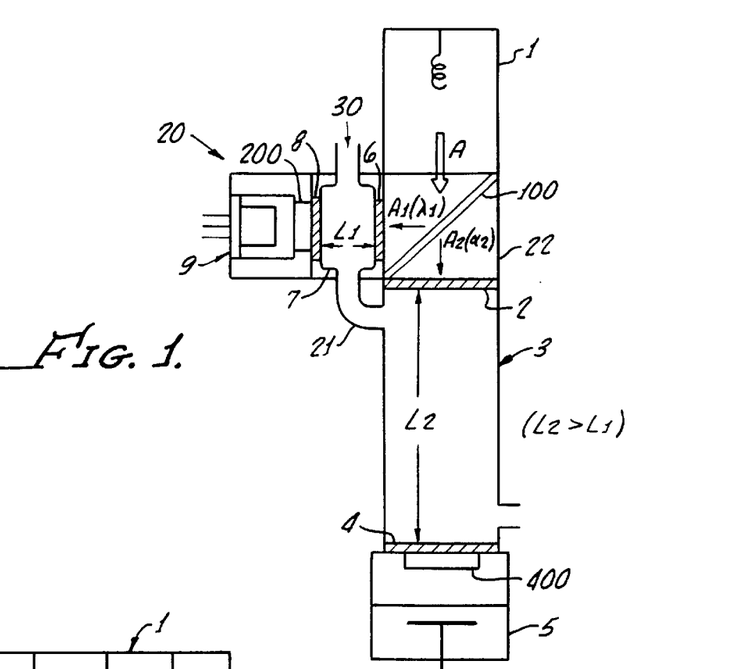
FIG. 1 is a schematic view showing a first embodiment of the present invention.

FIG. 1 shows a two-component measuring gas analyzer (NDIR) in which a $NO_X$ measuring cell having a cell length ($L_2$) of about 60 mm and a $CO_2$ measuring cell having a cell length ($L_1$) of about 1 mm are allowed to communicate with each other through a single gas path. In FIG. 1, a plurality of measuring cells 7 (a second cell), 3 (a first cell) whose cell lengths $L_1$, $L_2$ are different from each other communicate through a communication part 21 with each other to form a single gas path. A cut-on filter (optical filter) 100 as an infrared penetration/reflection means for diffracting spectrally an infrared wavelength is positioned adjacent to a light source 1. The $NO_X$ measuring cell 3 having a cell length $L_2$ and the $CO_2$ measuring cell 7 having a cell length L, which communicate through the communication part 21 with each other, and a capacitor microphone (an infrared-ray detector for $NO_X$) 5 and a peroelectric detector (an infrared-ray detector for $CO_2$) 9 are provided on the respective infrared penetration and reflection sides of the optical filter 100. This embodiment employs a fluid-modulation (gas-modulation) system in which a sample gas 30 and a reference gas (not shown) are alternately supplied to the measuring cells 3, 7.

Although in this embodiment the cut-on filter 100 is built in a gas filter cell 22 formed with an interference-component gas filled, the filter is not always filled with the interference-component gas, and may be set as appropriate.

The measuring operation will be explained hereinafter. The sample gas 30 (or the reference gas) passes from the measuring cell 7 through the communication part 21 to the measuring cell 3. The flow direction of the sample gas may be made reverse. On the other hand, infrared rays A emitted from the light source 1 are divided into a reflected light $A_1$ ($\lambda_1$) and a penetrated light $A_2$ ($\lambda_2$) by the cut-on filter 100 having absorbency characteristics shown by the curve P in FIG. 8. That is, the reflected light $A_1$ ($\lambda_1$) has a short wavelength $\lambda_1$ ($\leq a$) shorter than $CO_2$ absorption wavelength a ($\approx 4.3\,\mu m$), while the penetrated light $A_2$ (>a) other than the wavelength.

Figure 8:
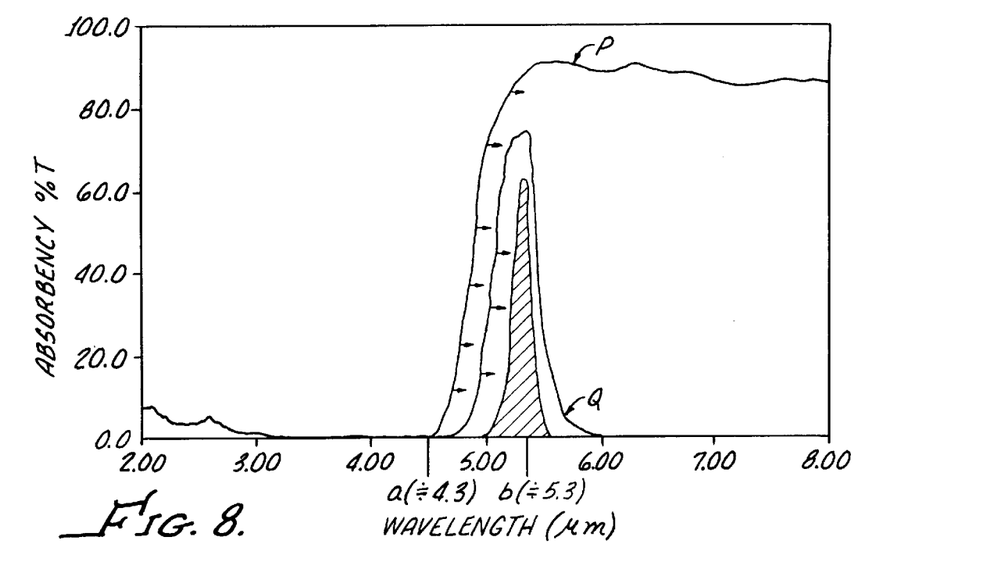
FIG. 8 is a characteristic graph showing the spectral wavelength characteristics of an infrared penetration/reflection means used in the present invention.

For the penetrated light $A_2$, during the period when the light passes through a $CaF_2$ window 2 provided on one end and then through the $NO_X$ measuring cell 3 having a cell length $L_2$ of about 60 mm, the component gas to be measured in the measuring cell absorbs infrared rays, and after the light passes through a $CaF_2$ window 4 provided on the other end, only the absorption wavelength b($\approx 5.3\,\mu m$) in the $NO_X$ gas passes through an NO band-pass filter 400 having absorbency characteristics shown by the curve Q in FIG. 8 and then reaches a $NO_X$ detector 5. On the other hand, the reflected light $A_1$ passes through a $CaF_2$ window 6 and through the $CO_2$ measuring cell 7 where the component gas to be measured absorbs infrared rays, and then through a $CaF_2$ window 8, and thereafter only the absorption wavelength a ($\approx 4.3\,\mu m$) in the $CO_2$ gas passes through a $CO_2$ band-pass filter 200 having absorbency characteristics shown by the curve R in FIG. 9 and then reaches a $CO_2$ detector 9.

As described above, in this embodiment, there are provided the two measuring cells 3, 7 having cell lengths $L_2$, $L_1$ adaptable to respective components (NO and $CO_2$), and these measuring cells are allowed to communicate with each other to form a single gas path. While the cut-on filter 100 is provided on the light source 1 side, the above-mentioned measuring cells 3, 7 communicating through the communicating part 21 with each other are arranged on the infrared penetration and reflection sides of the cut-on filter 100, and the detectors 5, 9 are provided for the respective measuring cells 3, 7, so that the two different components to be measured for the adaptable cell lengths $L_2$, $L_1$ can be measured by only the single path at a high accuracy.

Figure 2:
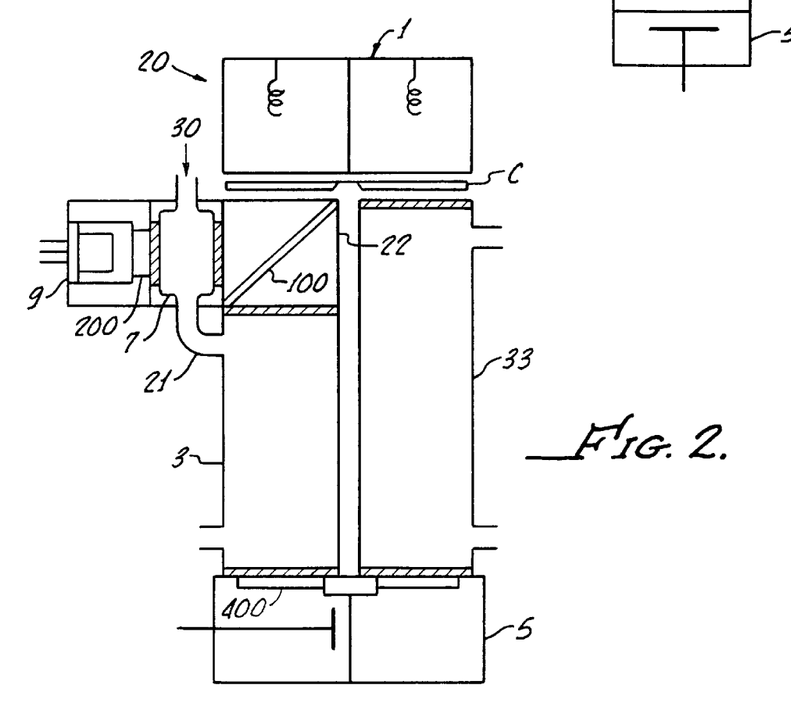
FIG. 2 is a schematic view showing a second embodiment of the present invention.

FIG. 2 is a light-intermittent (light-modulation) type NDIR 20 in which a rotary chopper (light intermitter) C for intermitting infrared rays from the light source 1 is provided between the light source 1 and a gas filter cell 22 so as to perform two components measurement as with the above-mentioned first embodiment, and shows a second embodiment of the present invention. Reference code 33 designates a reference cell filled with an inert gas such as $N_2$, and within the reference cell 33, the infrared rays from the light source 1 are not absorbed, so that a certain quantity of light reaches a two-chamber light reception type infrared-ray detector 5 at all times. For this reason, there occurs a difference in quantity of incident infrared rays between the measuring cell 3 and the reference cell 33, and both the infrared rays are intermitted by the rotary chopper 32, so that the capacitor microphone in the infrared-ray detector 5 vibrates. When a change in electrostatic capacity due to the vibration is picked up, the change thus picked up can be processed as a signal of $NO_2$ gas concentration.

Figures 3, 4:
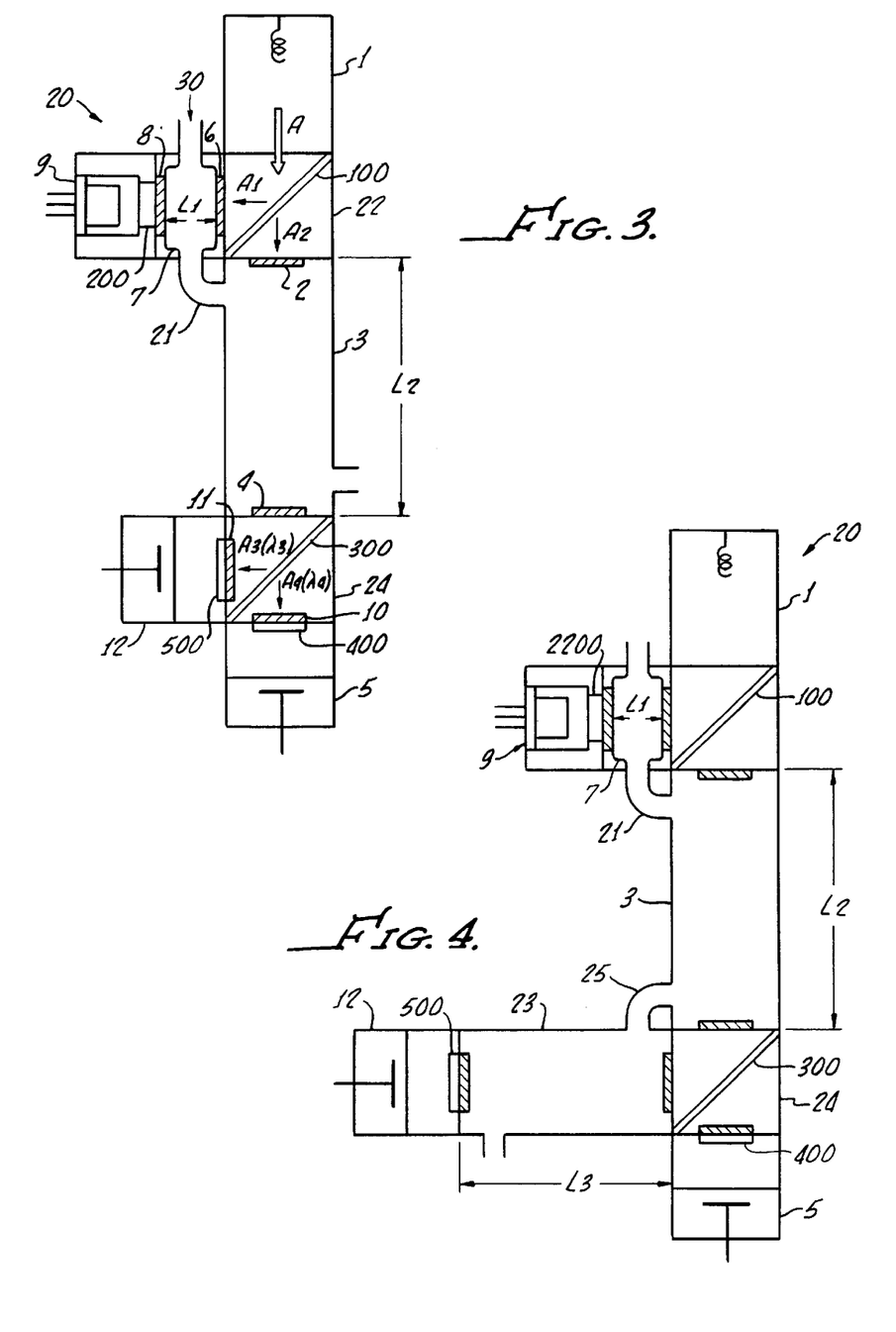
FIG. 3 is a schematic view showing a third embodiment of the present invention.
FIG. 4 is a schematic view showing a fourth embodiment of the present invention.

FIG. 3 shows a third embodiment in which a cut-on filter 100 as a first infrared penetration/reflection means for diffracting spectrally in infrared wavelength is provided on a light source 1 side. A $NO_X$ measuring cell 3 having a cell length $L_2$ of about 60 mm and a $CO_2$ measuring cell 7 having a cell length $L_1$ of about 1 mm which communicate through a communication part 21 with each other, and an infrared-ray detector 5 for $NO_X$ and an infrared-ray detector 9 for $CO_2$ are provided on the respective infrared penetration and reflection sides of the first optical filter 100. A $NO_X$ band-pass filter 300 as a second infrared penetration/reflection means is provided between the $NO_X$ measuring cell 3 and the infrared-ray detector 5 for $NO_X$. The infrared-ray detector 5 for $NO_X$ is provided on the infrared penetration side of the $NO_X$ band-pass filter 300. An infrared-ray detector 12 for $SO_2$ is provided on the infrared reflection side of the $NO_X$ band-pass filter 300, so that three components (NO, $CO_2$ and $SO_2$) are measured. Although in this embodiment, the $NO_X$ band-pass filter 300 is built in a gas filter cell 24 formed with an interference-component gas filled, the filter is not always filled with the interference-component gas, and may be set as appropriate. This embodiment through a seventh embodiment employ a fluid-modulation type NDIR 20 as with the above-mentioned first embodiment.

Figure 10:
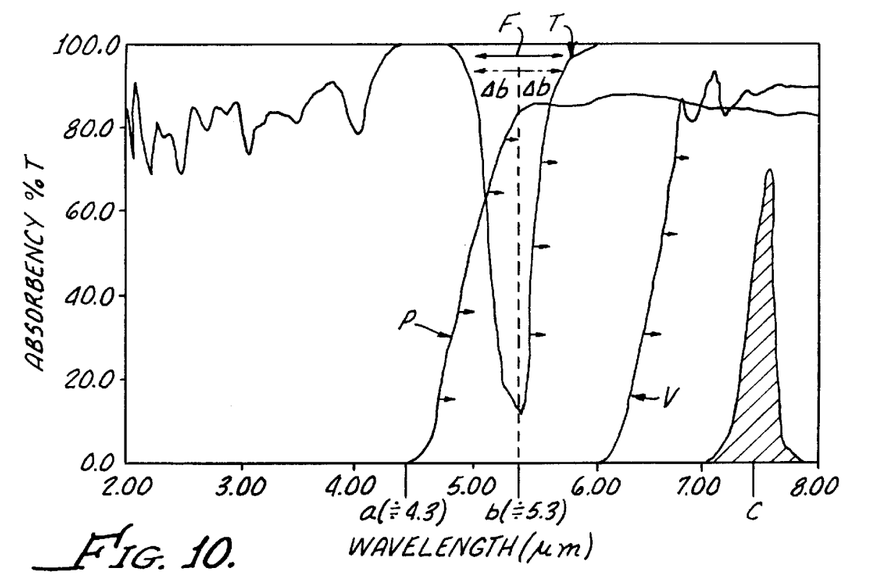
FIG. 10 is also a characteristic graph showing the spectral wavelength characteristics of an infrared penetration/reflection means used in the present invention.

The measuring operation will be explained hereinafter. With reference to FIG. 3, the measurement of three components (NO, $CO_2$ and $SO_2$) will be explained. This embodiment is characterized in that the $NO_X$ band-pass filter (reflection spectrum) 300 having absorbency characteristics shown by the curve T in FIG. 10 is used so that the penetrated light $A_2$ ($\lambda_2$) in the first and second embodiments shown in FIGS. 1 and 2 is divided into a reflected light $A_3$ ($\lambda_3$) and a penetrated light $A_4$ ($\lambda_4$), and the reflected light $A_4$ are allowed to be incident upon the infrared-ray detector 12 for $SO_2$ and the infrared-ray detector 5 for $NO_X$, respectively. That is, a sample gas 30 (or a reference gas) flows from the measuring cell 7 through the communication part 21 to the measuring cell 3. The flow direction of the sample gas 30 may be made reverse.

The above-mentioned penetrated light $A_2$ ($\lambda_2$) is divided into the reflected light $A_3$ ($\lambda_3$) and the penetrated light $A_4$ ($\lambda_4$) by the $NO_X$ band-pass filter (reflection spectrum) 300. That is, the penetrated light $A_4$ ($\lambda_4$) has a wavelength $\lambda_4$ (b−$\Delta$b≦$\lambda_4$≦b+$\Delta$b) of the range shown by the region F in FIG. 10, while the reflected light $A_3$ ($\lambda_3$) reflected from the $NO_X$ band-pass filter (reflection spectrum) 300 has a wavelength $\lambda_3$ (a<$\lambda_3$<b−$\Delta$b, b+$\Delta$b <$\lambda_3$) other than the wavelength. The penetrated light $A_4$ passes through a $CaF_2$ window 10 provided on one side of the $NO_X$ band-pass filter (reflection spectrum) 300, and then only the NO gas absorption wavelength b (≈5.3 μm) passes through an NO band-pass filter 400 having characteristics shown by the curve Q in FIG. 8 and reaches the infrared-ray detector 5. On the other hand, the reflected light $A_3$ passes through a $CaF_2$ window 11, and then only the $SO_2$ gas absorption wavelength b (≈7.3 μm) passes through an $SO_2$ band-pass filter 500 having characteristics shown by the curve V in FIG. 10 and reaches the $SO_2$ detector 12.

FIG. 4 shows a fourth embodiment in which an auxiliary measuring cell 23 is provided on the infrared reflection side of a second optical filter 300 so as to improve the sensitivity of an $SO_2$ detector 12, the measuring cell 23 being allowed to communicate through a communication part 25 with a measuring cell 3. This causes the cell length to be enlarged from ($L_2$) of the above-mentioned third embodiment to ($L_2$+$L_3$), that is, the cell length can be set at a larger one, thereby increasing the sensitivity of the $SO_2$ detector 12.

Figures 5, 6, 7:
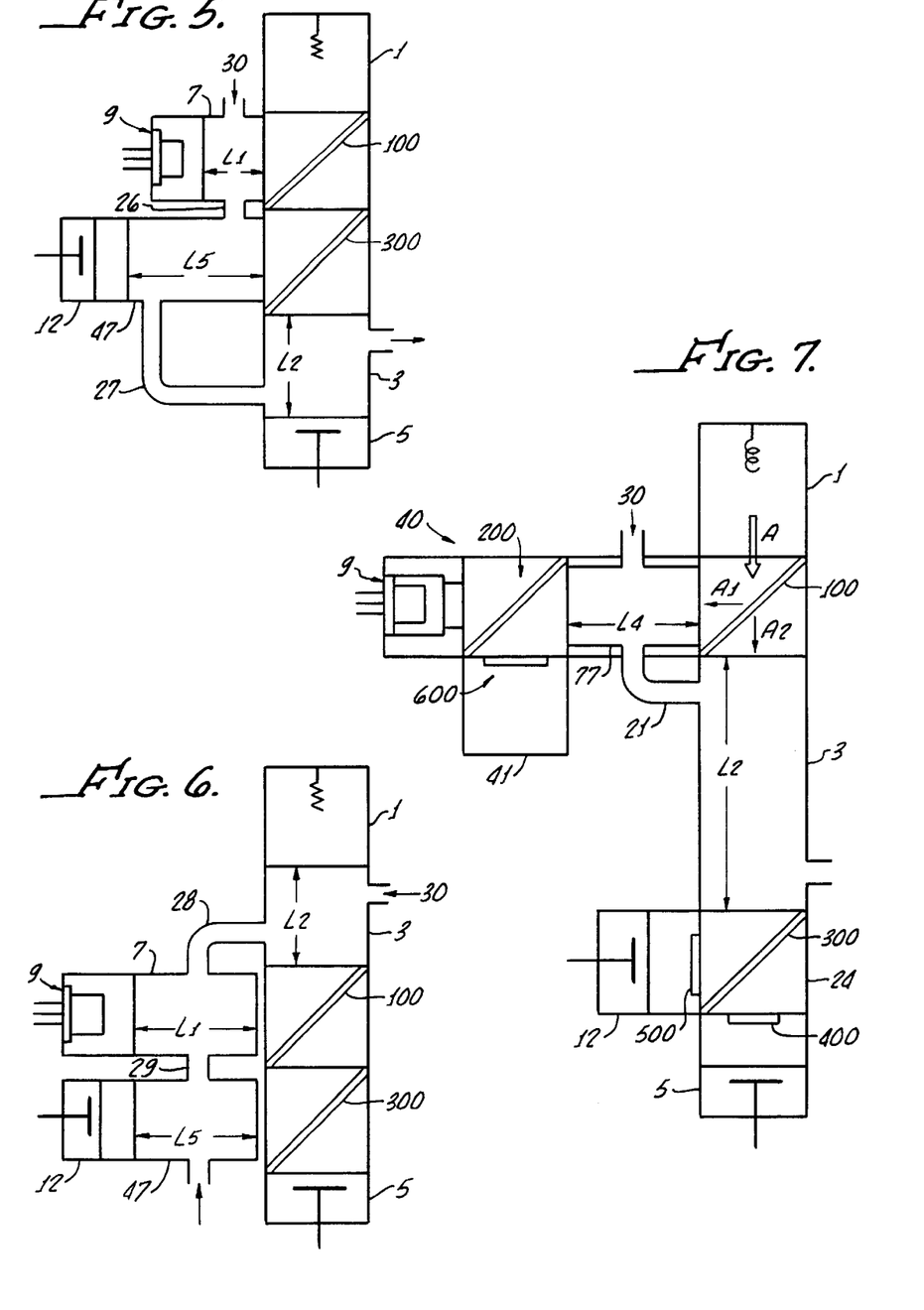
FIG. 5 is a schematic view showing a fifth embodiment of the present invention.
FIG. 6 is a schematic view showing a sixth embodiment of the present invention.
FIG. 7 is a schematic view showing a seventh embodiment of the present invention.

FIG. 5 shows a fifth embodiment in which a $NO_X$ band-pass filter (a second infrared penetration/reflection means) 300 is provided on one side (infrared penetration side) of a first infrared penetration/reflection means 100 positioned adjacent to a light source 1, while measuring cell 7 and an infrared-ray detector 9 are provided on the other side (infrared reflection side) of the first infrared penetration/reflection means 100. Another cell (a third cell having a cell length $L_5$) 47 allowed to communicate through a communication part 26 with a measuring cell 7 and an infrared-ray detector 12 are provided on the one side (infrared reflection side) of the second infrared penetration/reflection means 300, while a measuring cell 3 allowed to communicate through a communication part 27 with a measuring cell 47 and an infrared-ray detector 5 ar provided on the other side (infrared penetration side) of the second infrared penetration/reflection means 300, so as to measure three components. Although this embodiment has shown a composition in which the one side of the first infrared penetration/reflection means 100 is set at the infrared penetration side, while the one side of the second infrared penetration/reflection means 300 is set at the infrared reflection side, another composition may be employed in which the one side of the first infrared penetration/reflection means 100 is set at the infrared reflection side, while the one side of the second infrared penetration/reflection means 300 is set at the infrared penetration side.

FIG. 6 shows a sixth embodiment in which a measuring cell 3 and an infrared-ray detector 5 are provided on a light source side. A cut-on filter (a first infrared penetration/reflection means) 100 and a $NO_X$ band-pass filter (a second infrared penetration/reflection means) 300 are arranged between the measuring cell 3 and the infrared-ray detector 5. The second infrared penetration/reflection means 300 is provided serially on the one side (infrared penetration side) of the first infrared penetration/reflection means 100, and the infrared-ray detector 5 is provided on the one side (infrared penetration side) of the second infrared penetration/reflection means 300. A measuring cell 7 allowed to communicate through a communication part 28 with a measuring cell 3 and an infrared-ray detector 9 are provided on the other side (infrared reflection side) of the first infrared penetration/reflection means 100. A measuring cell (cell length $L_5$) 47 allowed to communicate through a communication part 29 with a measuring cell 7 and an infrared-ray detector 12 are provided on the other side (infrared reflection side) of the second infrared penetration/reflection means 300, so as to measure three components. Although this embodiment has shown a composition in which the one side of the first infrared penetration/reflection means 100 is set at the infrared penetration side, while the one side of the second infrared penetration/reflection means 300 is set at the infrared penetration side, another composition may be employed in which the one side of the first infrared penetration/reflection means 100 is set at the infrared reflection side, while the one side of the second infrared penetration/reflection means 300 is set at the infrared reflection side.

FIG. 7 shows a seventh embodiment in which a $CO_2$ band-pass filter 200 as a third infrared penetration/reflection means is added to the fluid-modulation type NDIR 20 of the third embodiment shown in FIG. 3 to measure four components (NO, $CO_2$, $SO_2$ and CO).

Figure 9:
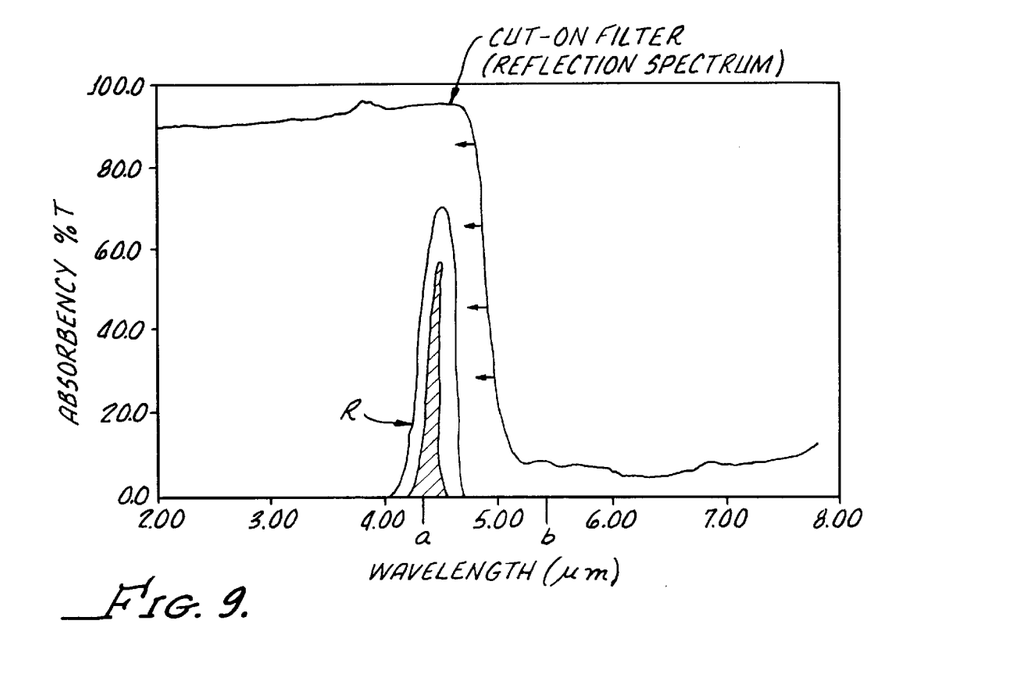
FIG. 9 is also a characteristic graph showing the spectral wavelength characteristics of an infrared penetration/reflection means used in the present invention.

In this embodiment, a cut-on filter (a first infrared penetration/reflection means) 100 for diffracting spectrally an infrared wavelength is provided on a light source 1 side. A $NO_X$ measuring cell 3 having a cell length $L_2$ of about 60 mm and a $CO_2$ measuring cell 77 having a cell length $L_1$ of about 1 mm which communicate through a communication part 21 with each other, and an infrared-ray detector 5 for $NO_X$ and an infrared-ray detector 9 for $CO_2$ are provided on the respective infrared penetration and reflection sides of the cut-on filter 100. A $NO_X$ band-pass filter (a second infrared penetration/reflection means) 300 is provided between the $NO_X$ measuring cell 3 and the infrared-ray detector 5 for $NO_X$. The infrared-ray detector 5 for $NO_X$ is provided on the infrared penetration side of the $NO_X$ band-pass filter 300, while an infrared-ray detector 12 for $SO_2$ is provided on the infrared reflection side of the $NO_X$ band-pass filter 300. A $CO_2$ band-pass filter 200 having characteristics shown by the curve R in FIG. 9 is provided between the infrared-ray detector 9 for $CO_2$ and the $CO_2$ measuring cell 77. The infrared-ray detector 9 for $CO_2$ is provided on the infrared penetration side of the $CO_2$ band-pass filter 200. An infrared-ray detector 41 for CO is provided through a CO band-pass filter 600 on the infrared reflection side of the $CO_2$ band-pass filter 200.

Figure 11:
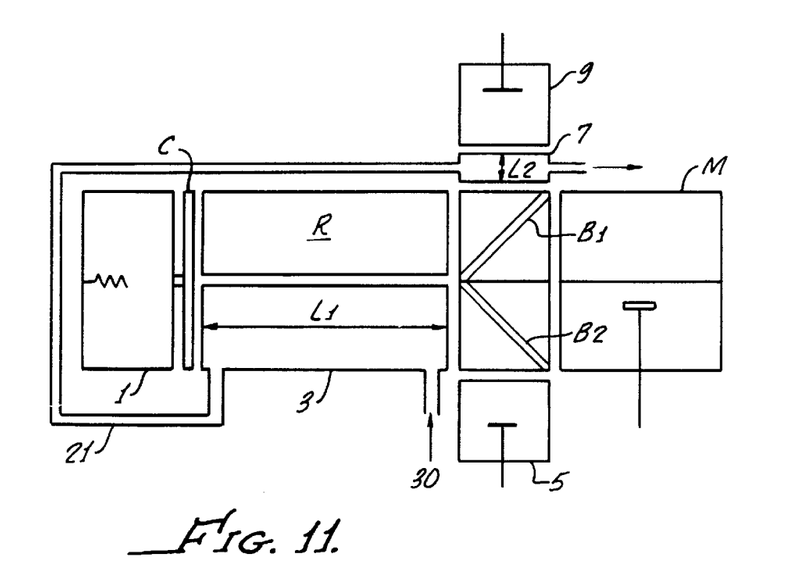
FIG. 11 is a schematic view showing an eighth embodiment of the present invention.

FIGS. 11 through 15 show other embodiments of the light-intermittent type NDIR 20. FIG. 11 shows an eighth embodiment in which a reference cell R together with a first infrared penetration/reflection means $B_1$ and a first measuring cell 3 together with a second infrared penetration/reflection means $B_2$ are provided parallel between a light intermitter C positioned adjacent to a light source 1 and a two-chamber reception type infrared-ray detector M. A first infrared-ray detector 5 is provided on the infrared reflection side of the above-mentioned second infrared penetration/reflection means $B_2$. A second infrared-ray detector 9 is provided through a second measuring cell 7 allowed to communicate with the above-mentioned first measuring cell 3 on the infrared reflection side of the above-mentioned first infrared penetration/reflection means $B_1$.

Figure 12:
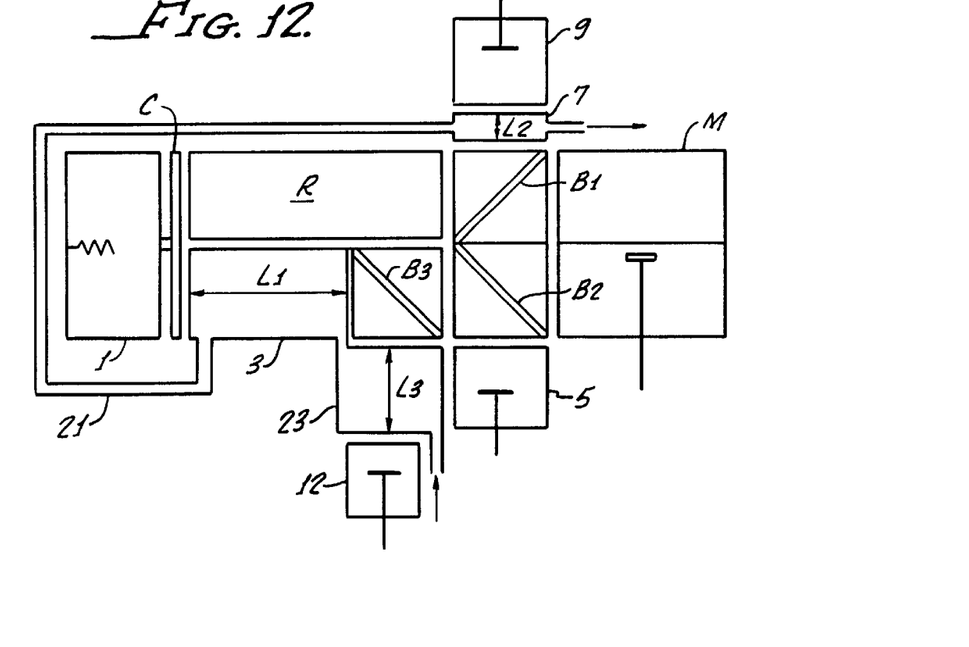
FIG. 12 is a schematic view showing a ninth embodiment of the present invention.

FIG. 12 shows a ninth embodiment in which a third infrared penetration/reflection means $B_3$ is arranged between a second infrared penetration/reflection means $B_2$ and a first measuring cell 3. A third measuring cell 23 communicating with the above-mentioned first measuring cell 3 is arranged on the infrared reflection side of the third infrared penetration/reflection means $B_3$. There is provided a third infrared-ray detector means 12 corresponding to the third measuring cell 23.

Figure 13:
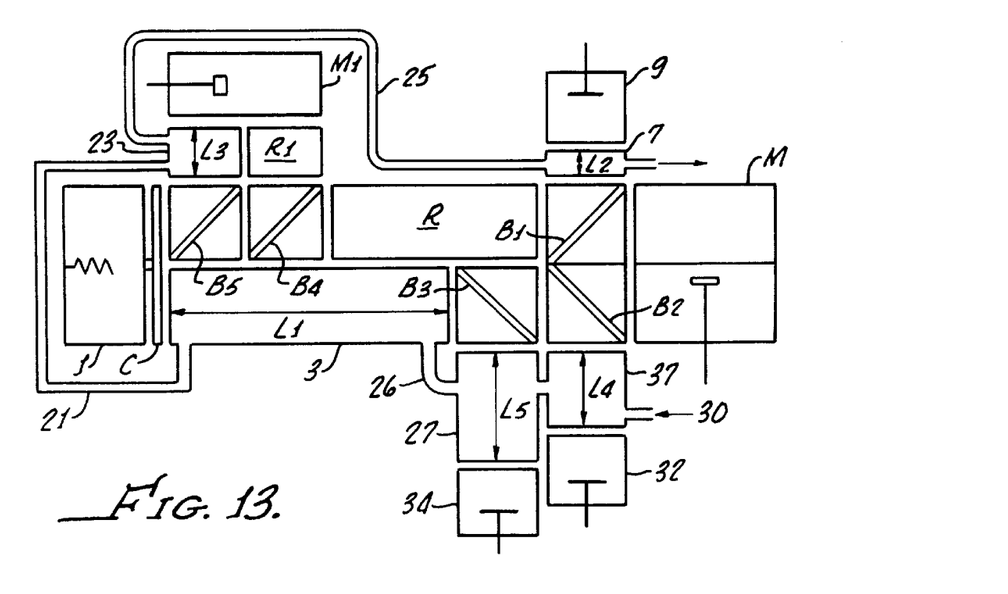
FIG. 13 is a schematic view showing a tenth embodiment of the present invention.

FIG. 13 shows a tenth embodiment in which one pair of infrared penetration/reflection means $B_4$, $B_5$ are provided between a light intermitter C and a reference cell R. A second reference cell $R_1$ is provided on the infrared reflection side of the infrared penetration/reflection means $B_4$, and the above-mentioned first measuring cell 3 and a third measuring cell 23 communicating with a second measuring cell 7 are provided on the infrared reflection side of the infrared penetration/reflection means $B_5$. There is provided a two-chamber light reception type infrared-ray detector $M_1$ corresponding to the second reference cell $R_1$ and the third measuring cell 23. Two infrared penetration/reflection means $B_2$, $B_3$ are provided between the first measuring cell 3 and a two-chamber light reception type infrared-ray detector M. Fourth and fifth measuring cells 37, 47 and infrared-ray detectors 32, 34 are arranged on the infrared reflection side thereof. Although in this case a sample gas flows from the fourth measuring cell 37 to the fifth measuring cell 47, the first measuring cell 3, the third measuring cell 23, and the second measuring cell 7, the flow direction may be made reverse.

Figure 14:
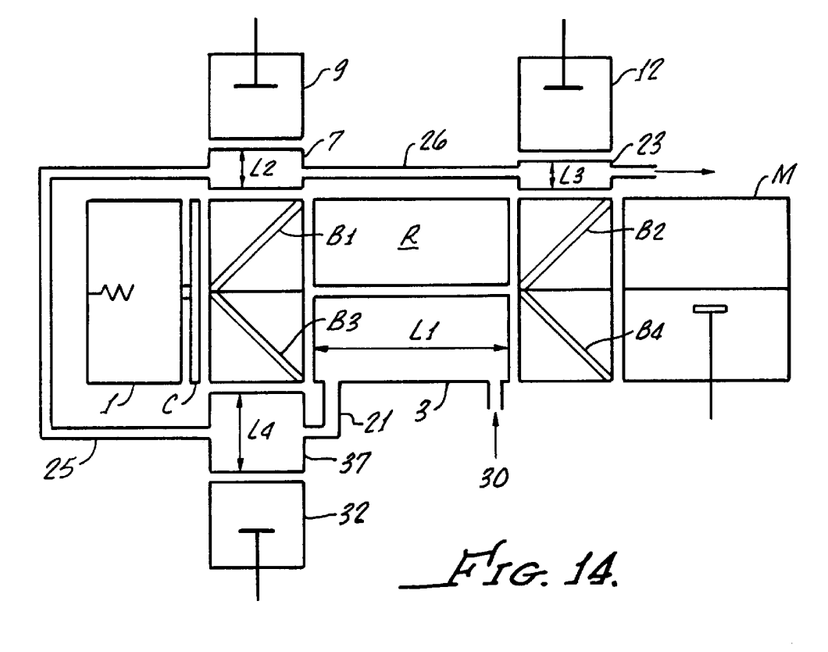
FIG. 14 is a schematic view showing an eleventh embodiment of the present invention.

FIG. 14 shows an eleventh embodiment in which a first infrared penetration/reflection means $B_1$, a reference cell R and a second infrared penetration/reflection means $B_2$ which are serially and adjacently arranged to each other and a third infrared penetration/reflection means $B_3$, a first measuring cell 3 and a fourth infrared penetration/reflection means $B_4$ which are serially and adjacently arranged to each other are provided parallel between a light intermitter C made adjacent to a light source 1 and a two-chamber light reception type infrared-ray detector M. A second measuring cell 7, a third measuring cell 23 and a fourth measuring cell 37 which communicate with the above-mentioned first measuring cell 3 and a second infrared-ray detector 9, a third infrared-ray detector 12 and a fourth infrared-ray detector 32 which correspond to respective measuring cells are provided on the respective infrared reflection side of the above-mentioned first infrared penetration/reflection means $B_1$, the second infrared penetration/reflection means $B_2$ and the third infrared penetration/reflection means $B_3$.

Figure 15:
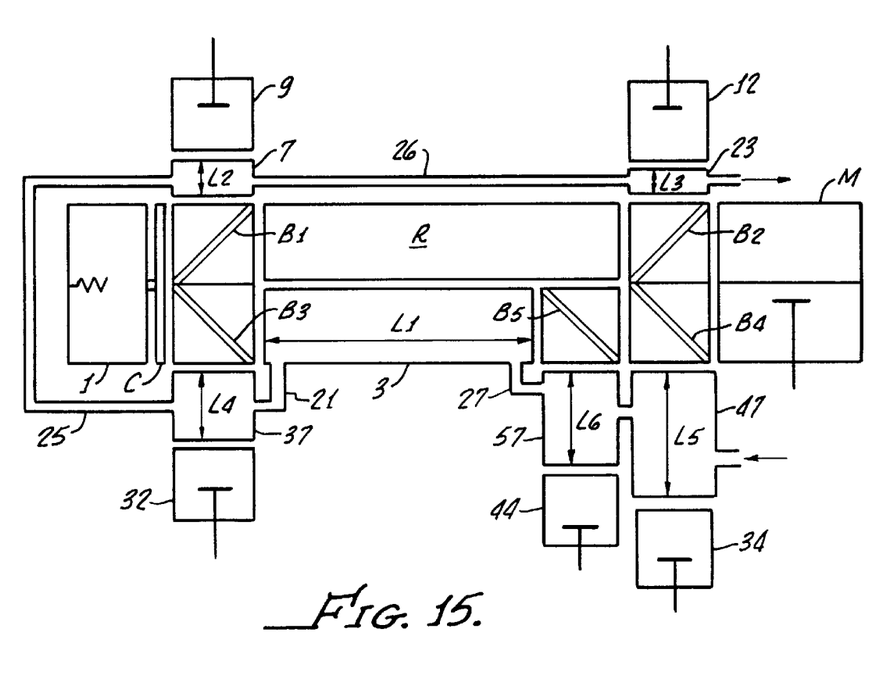
FIG. 15 is a schematic view showing a twelfth embodiment of the present invention.

In FIG. 15, a fifth infrared penetration/reflection means $B_5$ is provided adjacently between a fourth infrared penetration/reflection means $B_4$ and a first measuring cell 3. Measuring cells 47, 57 communicating with the above-mentioned first measuring cell 3 are provided on the respective infrared reflection sides of the fourth and fifth infrared penetration/reflection means $B_4$, $B_5$. There are provided infrared-ray detector means 34, 44 corresponding to the measuring cells 47, 57.

The action and effect in the embodiment shown in the above-mentioned FIGS. 11 through 15 are basically the same as the embodiments shown in the above-mentioned FIGS. 1 through 7, so that the explanation thereof will be omitted. It will be appreciated that the present invention is not limited to the above-mentioned embodiments. The combination of infrared penetration/reflection means, measuring cells and infrared-ray detectors may be changed and set as appropriate according to above-mentioned embodiments. Also, it is to be understood that the reference codes of the cell length $L_1$ and the like shown do not specify the length thereof, but indicate a case where the measuring cells are different in length from each other.

As described above, in the above-mentioned embodiments, there are provided measuring cells having cell lengths adaptable to respective components, and these measuring cells having cell lengths adaptable to respective components, and these measuring cells are allowed to communicate with each other to form a single gas path. One or a plurality of infrared penetration/reflection means are provided on the light source side. The above-mentioned measuring cells communicating through the communication part with each other are arranged on the infrared penetration and reflection sides of the infrared penetration/reflection means. The infrared-ray detectors are provided for the respective measuring cells, so that a plurality of components which are to be measured and have different concentrations can be measured by only the single path.

Although the above-mentioned embodiments have shown a composition in which there is used an optical filter as an infrared penetration/reflection means for diffracting spectrally an infrared wavelength, a half mirror or beam splitter for splitting the quantity of infrared rays may be used. In this case, it is preferable that the penetration/reflection planes have an inclined angle of 45° to the optical axis of respective cell and are provided within the gas filter cells. The ratio of splitting of the quantity of light to the detectors by the beam splitter is used usually at 1:1. However, where there is a difference in the sensitivity peculiar to detectors among them, the splitter whose reflectance has been adjusted is employed to use the ratio of 1:2 or more, thereby distributing the quantity of light corresponding to the detection sensitivity of the respective detectors.

As described above, according to the present invention, there are provided measuring cells having cell lengths adaptable to respective components to be measured and concentrations, and these measuring cells are allowed to communicate with each other to form a single gas path. Infrared penetration/reflection means are provided on a light source side. The above-mentioned measuring cells communicating though a communication part with each other are arranged on the infrared penetration and reflection sides of the infrared penetration/reflection means. The infrared-ray detectors are provided for the respective measuring cells, so that there is an effect that a plurality of components which are to be measured and require different adaptable measuring length can be measured by a simple composition of the single gas path at a high accuracy.

We claim:

1. A gas analyzer comprising:

a light source;

at least one infrared penetration/reflection means provided immediately adjacent to the light source and having an infrared penetration side and an infrared reflection side;

a plurality of measuring cells communicating sequentially with each other to form a single gas path; and a plurality of infrared-ray detectors;

at least one set of one of the measuring cells and one of the infrared-ray detectors being provided immediately adjacent to the infrared penetration side of the infrared penetration/reflection means, and at least one set of one of the measuring cells and one of the infrared-ray detectors being provided immediately adjacent to the infrared reflection side of the infrared penetration/reflection means.

2. The gas analyzer as set forth in claim 1 wherein:

each of the measuring cells has a cell length different from the other measuring cells.

3. A gas analyzer comprising:

a light source;

a first infrared penetration/reflection means provided adjacent to the light source and having an infrared penetration side and an infrared reflection side;

a plurality of measuring cells communicating sequentially with each other to form a single gas path;

a plurality of infrared-ray detectors, at least one set of one of the measuring cells and one of the infrared-ray detectors being provided on the infrared penetration side of the first infrared penetration/reflection means, and at least one set of one of the measuring cells and one of the infrared-ray detectors being provided on the infrared reflection side of the first infrared penetration/reflection means; and a second infrared penetration/reflection means having an infrared reflection side and an infrared penetration side provided between one of the measuring cells and the infrared-ray detector corresponding thereto;

one of the infrared-ray detectors being provided on the infrared reflection side of the second infrared penetration/reflection means for detecting infrared rays reflected by the second infrared penetration/reflection means.

4. The gas analyzer as set forth in claim 3 wherein:

one of the measuring cells is provided between the infrared reflection side of the second infrared penetration/reflection means and the infrared-ray detector provided on the same side, and is in communication with the plurality of measuring cells.

5. A gas analyzer comprising:

a light source;

a first infrared penetration/reflection means provided adjacent to the light source and having an infrared penetration side and an infrared reflection side;

a plurality of measuring cells communicating sequentially with each other to form a single gas path;

a plurality of infrared-ray detectors, at least one set of one of the measuring cells and one of the infrared-ray detectors being provided on the infrared penetration side of the first infrared penetration/reflection means, and at least one set of one of the measuring cells and one of the infrared-ray detectors being provided on the infrared reflection side of the first infrared penetration/reflection means; and a second infrared penetration/reflection means having an infrared reflection side and an infrared penetration side and being provided between the infrared penetration side of the first infrared penetration/reflection means and the set of one of the measuring cells and one of the infrared-ray detectors;

at least one set of one of the measuring cells and one of the infrared-ray detectors being provided on the infrared reflection side of the second infrared penetration/reflection means.

6. A gas analyzer comprising:

a light source;

a first infrared penetration/reflection means provided adjacent to the light source and having an infrared penetration side and an infrared reflection side:

a plurality of measuring cells communicating sequentially with each other to form a single gas path;

a plurality of infrared-ray detectors, at least one set of one of the measuring cells and one of the infrared-ray detectors being provided on the infrared penetration side of the first infrared penetration/reflection means, and at least one set of one of the measuring cells and one of the infrared-ray detectors being provided on the infrared reflection side of the first infrared penetration/reflection means;

one of the measuring cells being provided between the light source and the infrared penetration/reflection means; and a second infrared penetration/reflection means having an infrared reflection side and an infrared penetration side and being connectedly provided on the infrared penetration side of the first infrared penetration/reflection means;

at least one set of one of the measuring cells and one of the infrared-ray detectors being provided on the infrared reflection side of the second infrared penetration/reflection means.

7. A gas analyzer comprising:

a light source;

a first infrared penetration/reflection means provided adjacent to the light source and having an infrared penetration side and an infrared reflection side;

a plurality of measuring cells communicating sequentially with each other to form a single gas path;

a plurality of infrared-ray detectors, at least one set of one of the measuring cells and one of the infrared-ray detectors being provided on the infrared penetration side of the first infrared penetration/reflection means, and at least one set of one of the measuring cells and one of the infrared-ray detectors being provided on the infrared reflection side of the first infrared penetration/reflection means;

a second infrared penetration/reflection means having an infrared reflection side and an infrared penetration side and being provided between one of the measuring cells and the infrared-ray detector corresponding thereto;

one of the infrared-ray detectors being provided on the infrared reflection side of the second infrared penetration/reflection means for detecting infrared rays reflected by the second infrared penetration/reflection means; and a third infrared penetration/reflection means having an infrared reflection side and an infrared penetration side and being provided between another one of the measuring cells and the infrared-ray detector corresponding thereto;

one of the infrared-ray detectors being provided on the infrared reflection side of the third infrared penetration/reflection means for detecting infrared rays reflected by the third infrared penetration/reflection means.

8. A light-intermittent gas analyzer comprising:

a light source;

a light intermitter provided adjacent to the light source;

a plurality of infrared penetration/reflection means each having an infrared penetration side and an infrared reflection side;

a reference cell positioned between the light intermitter and a first infrared penetration/reflection means;

a plurality of measuring cells communicating sequentially with each other to form a single gas path, a first measuring cell being provided on the infrared reflection side of the first infrared penetration/reflection means, and a second measuring cell being provided between the light intermitter and a second infrared penetration/reflection means and substantially parallel to the reference cell;

a two-chamber light reception infrared-ray detector provided on the infrared penetration sides of the first and the second infrared penetration/reflection means; and a plurality of infrared-ray detectors, a first infrared-ray detector being provided on the infrared reflection side of the first infrared penetration/reflection means, and a second infrared-ray detector being provided on the infrared reflection side of the second infrared penetration/reflection means.

9. The light-intermittent gas analyzer as set forth in claim 8 wherein:

a third infrared penetration/reflection means is arranged between the second infrared penetration/reflection means and the second measuring cell;

a third measuring cell communicating with the first measuring cell is arranged on the infrared reflection side of the third infrared penetration/reflection means; and a third infrared-ray detector is provided on the infrared reflection side of the third measuring cell.

10. The light-intermittent gas analyzer as set forth in claim 9 wherein:

at least one pair of infrared penetration/reflection means are provided between said light intermitter and the reference cell;

a second reference cell being provided on the infrared reflection side of the infrared penetration/reflection means;

the first measuring cell and a third measuring cell communicating with the second measuring cell are provided on the infrared reflection side of the infrared penetration/reflection means; and a second two-chamber light reception type infrared-ray detector corresponding to the second reference cell and the third measuring cell is provided.

11. The light-intermittent gas analyzer as set forth in claim 8 wherein:

at least one pair of infrared penetration/reflection means are provided between said light intermitter and the reference cell;

a second reference cell is provided on the infrared reflection side of the infrared penetration/reflection means;

the first measuring cell and a third measuring cell communicating with the second measuring cell being proved on the infrared reflection side of the infrared penetration/reflection means; and a second two-chamber light reception type infrared-ray detector corresponding to the second reference cell and the third measuring cell.

12. The light-intermittent gas analyzer as set forth in claim 8 wherein:

a third infrared penetration/reflection means is arranged between the reference cell and the light intermitter;

a fourth infrared penetration/reflection means is arranged between the second measuring cell and the light intermitter;

a third infrared-ray detector and a third measuring cell are provided on the infrared reflection side of the third infrared penetration/reflection means; and a fourth infrared-ray detector and a fourth measuring cell are provided on the infrared reflection side of the fourth infrared penetration/reflection means.

13. The light-intermittent gas analyzer as set forth in claim 12 wherein:

a fifth measuring cell in communication with the first measuring cell and a fifth infrared-ray detector are provided on the infrared refection side of the second penetration/reflection means.

14. The light-intermittent gas analyzer as set forth in claim 13 wherein at least one infrared penetration/reflection means is provided between the first measuring cell and the second penetration/reflection means;

a measuring cell communication with the first measuring cell in combination with an infrared-ray detector are provided on the infrared refection side of each infrared penetration/reflection means provided between the first measuring cell and the second penetration/reflection means.

15. The light-intermittent gas analyzer as set forth in claim 12 wherein:

at least one infrared penetration/reflection means is provided between the first measuring cell and the second penetration/reflection means;

a measuring cell communication with the first measuring cell in combination with an infrared-ray detector are provided on the infrared reflection side of each infrared penetration/reflection means provided between the first measuring cell and the second penetration/reflection means.

16. The light-intermittent gas analyzer as set forth in claim 8 wherein:

each of the measuring cells has a cell length different from the other measuring cells.

* * * * *

UNITED STATES PATENT AND TRADEMARK OFFICE
CERTIFICATE OF CORRECTION

PATENT NO. : 5,773,828
DATED : June 30, 1998
INVENTOR(S) : Shigeyuki Akiyama; Masahiko Fujiwara; Takuji Oida; Naohito Shimizu; Aritoshi Yoneda; Toshikazu Ohnishi It is certified that error appears in the above-indentified patent and that said Letters Patent is hereby corrected as shown below:

Column 11, line 55, between the words "side" and "provided" insert the word --being--.

Signed and Sealed this

Sixth Day of October, 1998

Attest:

BRUCE LEHMAN

Attesting Officer

Commissioner of Patents and Trademarks